United States Patent [19]

Crenshaw et al.

[11] E Re. 31,588

[45] Reissued May 22, 1984

[54] IMIDAZOLYLMETHYLTHIOETHYL ALKYNYL GUANIDINES

[75] Inventors: Ronnie R. Crenshaw, Dewitt; George M. Luke, Lafayette, both of N.Y.

[73] Assignee: Bristol-Myers Company, New York, N.Y.

[21] Appl. No.: 274,291

[22] Filed: Jun. 16, 1981

Related U.S. Patent Documents

Reissue of:

[64] Patent No.: 4,112,234
Issued: Sep. 5, 1978
Appl. No.: 848,959
Filed: Nov. 7, 1977

U.S. Applications:

[63] Continuation-in-part of Ser. No. 826,796, Aug. 22, 1977, abandoned, which is a continuation-in-part of Ser. No. 803,009, Jun. 3, 1977, abandoned.

[51] Int. Cl.[3] ..... C07D 233/64

[52] U.S. Cl. ..... 548/342; 260/453.4; 424/273 R

[58] Field of Search ..... 548/342

[56] References Cited

U.S. PATENT DOCUMENTS

| | | | |
|---|---|---|---|
| 3,501,497 | 3/1970 | Bell | 260/326.11 |
| 3,736,331 | 5/1973 | Black et al. | 260/309 |
| 3,825,547 | 7/1974 | Loev | 260/294.5 E |
| 3,860,592 | 1/1975 | Loev | 260/247.1 M |
| 3,881,015 | 4/1975 | Black et al. | 424/273 |
| 3,894,151 | 7/1975 | Black et al. | 424/246 |
| 3,897,555 | 7/1975 | Loev | 424/263 |
| 3,898,335 | 8/1975 | Loev | 424/248 |
| 3,950,333 | 4/1976 | Durant et al. | 544/224 |
| 3,950,522 | 4/1976 | Loev | 424/248 |
| 3,954,982 | 4/1976 | Black et al. | 424/246 |
| 3,956,494 | 5/1976 | Loev | 424/251 |
| 4,000,302 | 12/1976 | Black et al. | 424/273 R |
| 4,058,557 | 10/1977 | Douglas et al. | 260/501.14 |
| 4,100,349 | 7/1978 | Metcalf et al. | 548/337 |
| 4,157,340 | 6/1979 | Crenshaw et al. | 260/453.4 |
| 4,157,347 | 6/1979 | Crenshaw et al. | 260/453.4 |
| 4,158,013 | 6/1979 | Crenshaw et al. | 260/453.4 |
| 4,200,578 | 4/1980 | Algieri et al. | 548/193 |
| 4,200,760 | 4/1980 | Algieri et al. | 548/342 |
| 4,204,000 | 5/1980 | Diamond et al. | 424/304 |

FOREIGN PATENT DOCUMENTS

| | | |
|---|---|---|
| 804144 | 2/1974 | Belgium . |
| 841814 | 10/1976 | Belgium . |
| 843840 | 1/1977 | Belgium . |
| 2038798 | 7/1980 | United Kingdom . |

OTHER PUBLICATIONS

*Bull. Soc. Chim. Fr.*, 490 (1958).
*Bull. Soc. Chim. Fr.*, 592 (1967).
*Annales de Chemie* (Paris) 3, 656 (1958).
*J. Org. Chem.* 32, 1566 (1967).
*J. Int. Med. Res.* 3, 86 (1975).
*Lancet*, 1 (8001), 4 (1977).
*Nature* 236, 385 (1972).
*Proc. Soc. Exp. Biol. Med.* 148, 127 (1975).
*J. Pharmacol. Exp. Ther.* 200, 352 (1970).
*Agents and Actions*, 3, 133 (1973).
*Fed Proc.* 35, 1931 (1976).
*Agents and Actions*, 4, 217 (1974).
*Gastroentorology* 5, 53 (1945).
*Gastroentorology* 26, 906 (1954).
*Am. J. Dig. Dis.* 11, 231 (1966).
*Proc. Soc. Exp. Biol. Med.* 46, 260 (1941).
Ganellin et al, Federation Proceedings, (1976), vol. 35, pp. 1924–1930.
Drugs of the Future, 1976, vol. 1, pp. 13–18.
*Gastroentorology* 66, 517 (1974).

*Primary Examiner*—Richard A. Schwartz
*Attorney, Agent, or Firm*—Fitzpatrick, Cella, Harper & Scinto

[57] ABSTRACT

Compounds of the formula

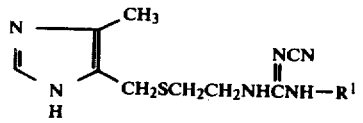

wherein $R^1$ is a straight or branched chain alkynyl group containing from 3 to 9 carbon atoms, inclusive, and nontoxic pharmaceutically acceptable acid addition salts thereof, are potent anti-ulcer agents.

10 Claims, No Drawings

IMIDAZOLYLMETHYLTHIOETHYL ALKYNYL GUANIDINES

Matter enclosed in heavy brackets [ ] appears in the original patent but forms no part of this reissue specification; matter printed in italics indicates the additions made by reissue.

CROSS-REFERENCE TO RELATED APPLICATION

This application *is a reissue of our application Ser. No. 848,959, now U.S. Pat. No. 4,112,234, which* is a continuation-in-part of our copending application, Ser. No. 826,796, filed Aug. 22, 1977, now abandoned, which in turn was a continuation-in-part of our application Ser. No. 803,009, filed June 3, 1977, and now abandoned.

SUMMARY OF THE INVENTION

This application relates to certain N-cyano-N'-{2-[(4-methyl-5-imidazolyl)methylthio]ethyl}-N''-alkynylguanidines which are $H_2$ receptor blocking agents, which inhibit gastric acid secretion and which are useful in the treatment of ulcers.

BACKGROUND AND PRIOR ART

The clinical objective in treatment of peptic ulcer disease is to decrease gastric acid secretion, based on the principle "no acid, no ulcer." Traditional peptic ulcer disease therapy involves control of diet and the use of antacids and anticholinergics.

There is evidence indicating that histamine may be the final common pathway for stimulation of gastric secretion. This effect of histamine is mediated via $H_2$ receptors and is not inhibited by the classical antihistamines, which are $H_1$ receptor blockers. A number of specific $H_2$ receptor blocking agents ($H_2$ receptor antagonists) are now known. These compounds inhibit basal acid secretion, as well as secretion by other known gastric acid stimulants, and are useful in the treatment of peptic ulcers.

Burimamide (IIa) was the first clinically effective $H_2$ receptor antagonist. It inhibits gastric secretion in animals and man, but oral absorption is poor.

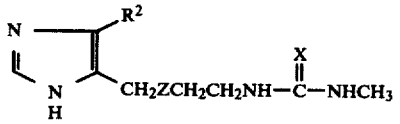

IIa; $R^2$=H, Z=$CH_2$, X=S Burimamide
b; $R^2$=$CH_3$, Z=S, X=S Metiamide
c; $R^2$=$CH_3$, Z=S, X=NCN Cimetidine Metiamide (IIb), a subsequently evaluated $H_2$ antagonist, is more potent than burimamide and is orally active in man. Clinical utility was limited, however, owing to toxicity (agranulocytosis). Cimetidine (IIc) is as effective an $H_2$ antagonist as metiamide, without producing agranulocytosis, and has recently been marketed as an anti-ulcer drug. The half-life of cimetidine is relatively short, thereby necessitating a therapeutic regimen of multi daily doses of 200 mg. tablets. There is thus a need for anti-ulcer agents which are longer acting and/or more potent than cimetidine.

Reviews on the development of $H_2$ antagonists, including those discussed in the preceding paragraph, may be found in C. R. Ganellin, et al., Federation Proceedings, 35, 1924 (1976), in Drugs of the Future, 1, 13 (1976), and in references cited therein. Relevant patents are as follows:

1. U.S. Pat. No. 3,950,333 discloses inhibitors of histamine-stimulated gastric secretion having the formula

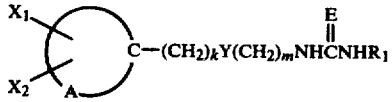

wherein A, taken together with the carbon atom, represents an unsaturated heterocyclic ring containing at least one nitrogen and may contain an additional hetero atom such as sulfur or oxygen, $X_1$ is inter alia (lower)alkyl, $X_2$ is inter alia hydrogen, k is 0 to 2, m is 2 or 3, provided that the sum of k and m is 3 or 4, Y is oxygen, sulfur or NH, E is $NR_2$ in which $R_2$ is hydrogen, nitro or cyano, and $R_1$ is hydrogen, (lower)alkyl or di(lower-)alkylamino-(lower)alkyl.

2. Belgian Pat. No. 804,144 (Farmdoc 19437V) discloses inhibitors of histamine-stimulated gastric acid secretion having the formula

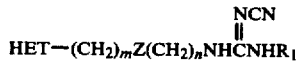

in which HET is a 5 or 6 membered heterocyclic ring containing nitrogen, which may be substituted inter alia by alkyl, m and n are 0–4 and the sum of m and n is from 2 to 4, Z is sulfur, oxygen, NH or $CH_2$, and $R_1$ is hydrogen or (lower)alkyl.

3. Belgian Pat. No. 841,814 (Farmdoc 90568X) discloses inhibitors of histamine-stimulated gastric secretion having the formula

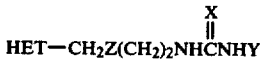

in which HET is one of eight named heterocyclic rings (including imidazole) which may be substituted inter alia by (lower)alkyl, Z is sulfur or $CH_2$, X is S, $CHNO_2$, NCN or NH, Y is $NH_2$, (lower)alkylamino, di(lower)alkylamino, (lower)alkoxy, phenylethyl, imidazolylethyl, allyl, trifluoroethyl or $(CH_2)_nR$ in which n is 1–12 and R is OH, (lower)alkoxy, $NH_2$ or (lower)alkylamino; provided that, when X is NH, Y is trifluoroethyl or $(CH_2)_nR$; and when X is NCN, Y may not be amino or (lower)alkyl.

This patent exemplifies and specifically claims the alkenyl compound of the formula

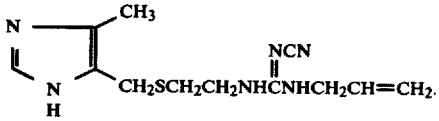

4. U.S. Pat. No. 3,894,151 discloses methods of inhibiting $H_1$ and $H_2$ histamine receptors, and compositions containing an antihistamine plus an $H_2$ histamine receptor inhibitor, wherein the $H_2$ histamine inhibitor is selected from the following groups:

(a) Thioureas of the formula

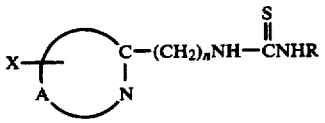

wherein A, taken together with the carbon and nitrogen, is an unsaturated heterocyclic ring, X is inter alia (lower)alkyl, n is 3–6, and R is hydrogen, (lower)alkyl, benzoyl or optionally substituted phenylethyl.

(b) Compounds of the formula

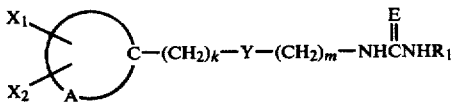

wherein A, taken together with the carbon, is an unsaturated heterocyclic ring containing at least one nitrogen, $X_1$ is inter alia (lower)alkyl, $X_2$ is inter alia hydrogen, k is 0 to 2 and m is 2–3, provided that the sum of k and m is 3 or 4, Y is oxygen, sulfur or NH, E is oxygen, sulfur or $NR_2$ in which $R_2$ is hydrogen, nitro or cyano, and $R_1$ is hydrogen, (lower)alkyl, benzoyl or di(lower)alkylamino-(lower)alkyl.

(c) Amidine derivatives of the formula

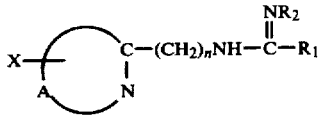

wherein A, taken together with the carbon and nitrogen, is an unsaturated 5–6 membered heterocyclic ring, X is inter alia (lower)alkyl, n is 2–5, $R_1$ is inter alia (lower)alkyl; $—NHR_3$ or $—SR_4$, $R_2$ is inter alia alkyl containing from 1–4 carbons or, when $R_1$ is $—NHR_3$, cyano or nitro, $R_3$ is inter alia hydrogen, methyl or amino, $R_4$ is inter alia alkyl containing 1–6 carbons or alkenyl or alkynyl containing 2–6 carbons.

(d) Isothioureas having the formula

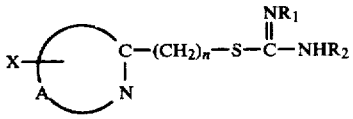

wherein A, taken together with the carbon and nitrogen, is an unsaturated 5 or 6 membered heterocyclic ring, X is hydrogen, halogen or benzyl, n is 2–4, $R_1$ is hydrogen or (lower)alkyl, $R_2$ is hydrogen, (lower)alkyl, amino or benzyl, or $R_1$ and $R_2$ taken together form an ethylene bridge.

(e) Amidines of the formula

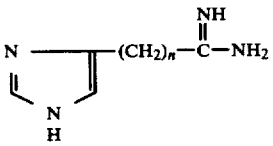

wherein n is 3 or 4.

The disclosures of U.S. Pat. Nos. 3,954,982 (a divisional of the above) and 4,000,302 (a continuation-in-part of the above) are substantially the same as that of U.S. Pat. No. 3,894,151.

5. Belgian Pat. No. 843,840 (Farmdoc 05613Y) discloses histamine $H_2$ receptor antagonists having the formula

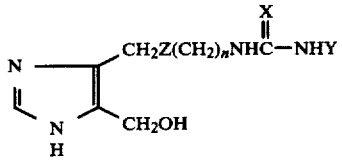

wherein n is 2–3, Z is sulfur or $CH_2$, Y is inter alia lower alkyl, and X is inter alia NCN.

Numerous other inhibitors of gastric acid secretion are known, but are considered much less relevant than those cited above because of still greater differences in structure from the instantly claimed compounds. The following patent covers compounds which are grossly different in structure from those claimed herein, but is cited as an example of compounds including alkynyl groups.

6. U.S. Pat. No. 3,897,555 discloses compounds of the formula

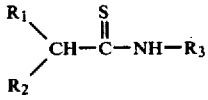

wherein $R_1$ is one of 8 named heterocyclic rings (not including imidazole), $R_2$ is inter alia hydrogen, (lower)alkyl, (lower)alkenyl or allyloxy, $R_3$ is an allyl or propargyl group which may be substituted by methyl or ethyl groups, said $R_3$ having 3–6 carbon atoms.

COMPLETE DISCLOSURE

This invention relates to histamine $H_2$ receptor antagonists which are effective inhibitors of gastric secretion in animals, including man, which are useful in the treatment of peptic ulcer disease, and which have the formula

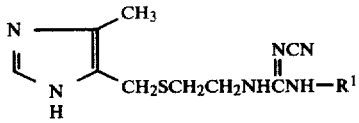

wherein $R^1$ is a straight or branched chain alkynyl group containing from 3 to 9 carbon atoms, inclusive, or nontoxic pharmaceutically acceptable acid addition salts thereof.

A preferred embodiment of the invention is a compound of the formula

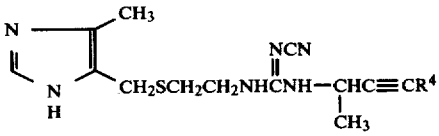

wherein $R^4$ is hydrogen or methyl, or a nontoxic pharmaceutically acceptable acid addition salt thereof.

Another preferred embodiment of the invention is a compound of the formula

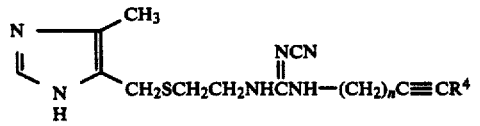

wherein $R^4$ is hydrogen or methyl and n is an integer of from 1 to 6, inclusive, or a nontoxic pharmaceutically acceptable acid addition salt thereof.

Another preferred embodiment of the invention is a compound of the formula

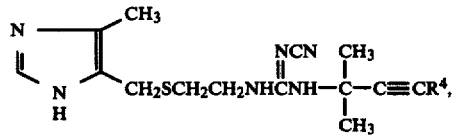

wherein $R^4$ is hydrogen or methyl, or a nontoxic pharmaceutically acceptable acid addition salt thereof.

A more preferred embodiment of the invention is N-cyano-N'-{2-[(4-methyl-5-imidazolyl)methylthio]ethyl}-N''-(2-butyn-1-yl)guanidine or a nontoxic pharmaceutically acceptable acid addition salt thereof.

Another more preferred embodiment of the invention is N-cyano-N'-{2-[(4-methyl-5-imidazolyl)methylthio]ethyl}-N''-(3-butyn-1-yl)guanidine or a nontoxic pharmaceutically acceptable salt thereof.

Another more preferred embodiment of the invention is N-cyano-N'-{2-[(4-methyl-5-imidazolyl)methylthio]ethyl}-N''-(4-pentyn-1-yl)guanidine or a nontoxic pharmaceutically acceptable acid addition salt thereof.

Another more preferred embodiment of the invention is N-cyano-N'-{2-[(4-methyl-5-imidazolyl)methylthio]ethyl}-N''-(2-methyl-3-butyn-2-yl)guanidine or a nontoxic pharmaceutically acceptable acid addition salt thereof.

Another more preferred embodiment of the invention is N-cyano-N'-{2-[(4-methyl-5-imidazolyl)methylthio]ethyl}-N''-(3-butyn-2-yl)guanidine or a nontoxic pharmaceutically acceptable acid addition salt thereof.

The most preferred embodiment of the invention is N-cyano-N'-{2-[(4-methyl-5-imidazolyl)methylthio]ethyl}-N''-propargyl guanidine or a nontoxic pharmaceutically acceptable acid addition salt thereof.

The compounds of the present invention may be prepared by several reaction schemes, as illustrated below for a preferred compound.

Scheme I

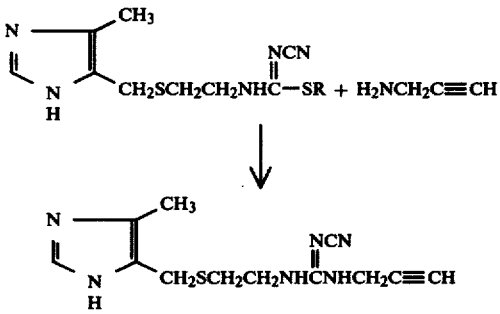

The reaction is conducted in a non-reactive solvent at a temperature above room temperature. As will be appreciated by those skilled in the art, R may be any substituent such that —SR will be a suitable leaving group. Thus, R may be (lower)alkyl, aryl, substituted aryl (e.g. p-nitrophenyl), aralkyl, —$CH_2CN$, —$CH_2COOH$, —$CH_2COOR'$, or the like. The N-cyano-N'-{2-[(4-methyl-5-imidazolyl)methylthio]ethyl}-S-R isothiourea starting materials may be prepared by the procedures described in Belgian Pat. No. 804,144. The alkynylamine starting materials are either commercially available or may be prepared by methods described in Bull. Soc. Chim. Fr., 490 (1958), Bull. Soc. Chim. Fr., 592 (1967) and Annales de Chimie (Paris), 3, 656 (1958).

Scheme II

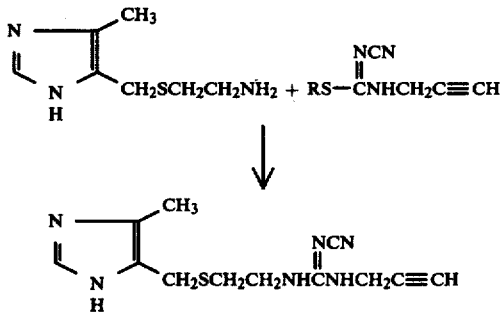

The reaction is conducted in a non-reactive solvent at a temperature above room temperature. The substituent R may be as indicated in Scheme I, above. The 2-[(4-methyl-5-imidazolyl)methylthio]ethylamine starting material may be prepared as described in U.S. Pat. No. 3,950,353. The disubstituted cyanodithioiminocarbonate which is used as a starting material for the preparation of the N-cyano-N'-propargyl-SR isothiourea (see step a of Example 2) may itself be prepared by procedures described in J. Org. Chem., 32, 1566 (1967)

Scheme III

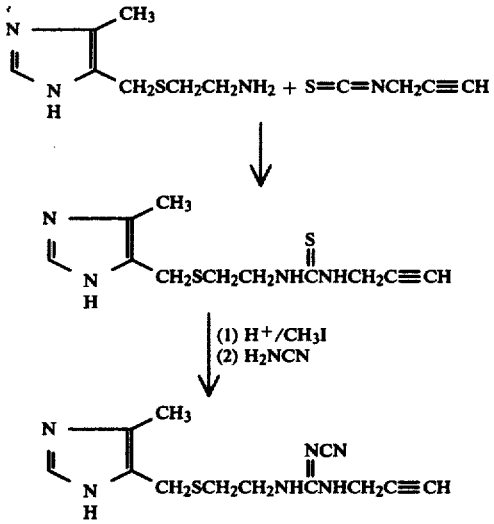

Scheme IV

-continued

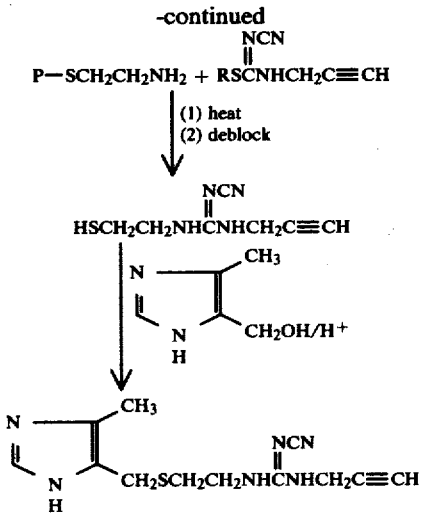

Substituent P may be any of the suitable sulfhydryl protecting groups known in the art.

As used herein, the term nontoxic pharmaceutically acceptable acid addition salt means the mono- or di-salt of a compound of this invention with a nontoxic pharmaceutically acceptable organic or inorganic acid. Such acids are well known and include hydrochloric, hydrobromic, sulfuric, sulfamic, phosphoric, nitric, maleic, fumaric succinic, oxalic, benzoic, methanesulfonic, ethanedisulfonic, benzenesulfonic, acetic, propionic, tartaric, citric, camphorsulfonic, and the like. The salts are made by methods known in the art.

For therapeutic use, the pharmacologically active compounds of this invention will normally be administered as a pharmaceutical composition comprising as the (or an) essential active ingredient at least one such compound in the basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or nonaqueous liquid suspension. The pharmaceutical compositions are prepared by conventional techniques appropriate to the desired preparation.

Preferably, each dosage unit will contain the active ingredient in an amount of from about 50 to about 250 mg., and most preferably from about 100 to about 200 mg.. The active ingredient will preferably be administered in equal doses from two to four times a day. The daily dosage regimen will preferably be from 250 to about 1000 mg., and most preferably from about 500 to about 750 mg..

Histamine $H_2$-receptor antagonists have been shown to be effective inhibitors of gastric secretion in animals and man, Brimblecombe et al., J. Int. Med. Res., 3, 86 (1975). Clinical evaluation of the chistamine $H_2$-receptor antagonist cimetidine has shown it to be an effective therapeutic agent in the treatment of peptic ulcer disease, Gray et al., Lancet, 1 (8001), 4 (1977). The compound prepared in Examples 1 and 2 below (hereinafter referred to as BL-5641) has been compared with cimetidine in various tests and has been shown to be more potent than cimetidine both as a histamine $H_2$-receptor antagonist in isolated guinea pig atria and as an inhibitor or gastric secretion in rats and dogs. Furthermore, the gastric secretion studies in dogs indicate that BL-5641 has a longer duration of activity than cimetidine at equal doses.

Histamine $H_2$-Receptor Antagonism-Isolated Guinea Pig Atria Assay

Histamine produces concentration-related increases in the contractile rate of isolated, spontaneously beating guinea pig right atria. Black et al., Nature, 236, 385 (1972), described the receptors involved in this effect of histamine as histamine $H_2$-receptors when they reported the properties of burimamide, a competitive antagonist of these receptors. Subsequent investigations by Hughes and Coret, Proc. Soc. Exp. Biol. Med., 148, 127 (1975) and Verma and McNeill, J. Pharmacol. Exp. Ther., 200, 352 (1977) support the conclusion of Black and coworkers that the positive chronotropic effect of histamine in isolated guinea pig right atria is mediated via histamine $H_2$-receptors. Black et al., Agents and Actions, 3, 133 (1973) and Brimblecombe et al., Fed. Proc., 35, 1931 (1976) have utilized isolated guinea pig right atria as a means for comparing the activities of histamine $H_2$-receptor antagonists. The present comparative studies were carried out using a modification of the procedure reported by Reinhardt et al., Agents and Actions, 4, 217 (1974).

Male Hartley strain guinea pigs (350–450 gm.) were sacrificed by a blow on the head. The heart was excised and placed in a Petri dish of oxygenated (95% $O_2$, 5% $CO_2$) modified Krebs solution (g./liter: NaCl 6.6, KCl 0.35, $MgSO_4 \cdot 7\,H_2O$ 0.295, $KH_2PO_4$ 0.162, $CaCl_2$ 0.238, $NaHCO_3$ 2.1 and dextrose 2.09). The spontaneously beating right atrium was dissected free from other tissues and a silk thread (4-0) attached to each end. The atrium was suspended in a 20 ml. muscle chamber containing oxygenated modified Krebs solution maintained at 32° C. Atrial contractions were recorded isometrically by means of a Grass FT 0.03 force displacement transducer and recordings of contractile force and rate were made with a Beckman RP Dynograph.

A resting tension of 1 g. was applied to the atrium and it was allowed to equilibrate for 1 hour. At the end of the equilibration period a submaximal concentration of histamine dihydrochloride ($3\times10^{-6}$M) was added to the bath and washed out to prime the tissue. Histamine was then added to the bath in a cumulative fashion using ½ log 10 intervals to give final molar bath concentrations of $1\times10^{-7}$ to $3\times10^{-5}$. The histamine-induced increase in atrial rate was allowed to plateau before the next successive concentration was added. The maximal response invariably occurred at the $3\times10^{-5}$M concentration. The histamine was washed out several times and the atrium allowed to return to control rate. The test compound ($1\times10^{-5}$M) was then added and after a 30 minute incubation the histamine concentration-response was repeated adding higher concentrations as needed.

The histamine ED50 values (concentration of histamine which increased contractile rate 50% of maximum) and 95% confidence limits before and after the test compound were obtained by regression analysis as described by Finney, Probit Analysis, 3rd ed., Cambridge (1971). Concentration-response curve displacement factors were calculated as follows:

$$\text{Displacement Factor} = \frac{\text{ED50 Histamine + Compound}}{\text{ED50 Histamine Alone}}$$

The factor obtained for BL-5641 was then expressed as a ratio of the factor obtained for cimetidine.

$$\text{Activity Ratio} = \frac{\text{BL-5641 Displacement Factor} - 1}{\text{Cimetidine Displacement Factor} - 1}$$

The results obtained from these studies are summarized in Table 1. Cimetidine and BL-5641 displaced the histamine concentration-response curve to the right by a factor of 6.6 and 32.7, respectively. Based on the concentration-response curve displacement factors, BL-5641 was about 5.7 times more active than cimetidine as a histamine $H_2$-receptor antagonist in isolated guinea pig right atria.

TABLE 1

Relative Activity of Cimetidine and BL-5641 in Isolated Guinea Pig Right Atria

| Compound | N | Concentration | Histamine ED50 With 95% Confidence Limits (μg/ml.) | Concentration-Response Curve Displacement Factor | Activity Ratio |
|---|---|---|---|---|---|
| Histamine Control | 3 | | 0.21 (0.18–0.25) | — | — |
| Cimetidine | 3 | $1 \times 10^{-5}$M | 1.39 (1.08–1.85) | 6.6 | 1.0 |
| Histamine Control | 2 | | 0.38 (0.27–0.53) | — | — |
| BL-5641 | 2 | $1 \times 10^{-5}$M | 12.44 (7.81–20.28) | 32.7 | 5.7 |

N = number of experiments.

Determination of Gastric Antisecretory Activity in the Two Hour Pylorus Ligated (Shay) Rat The pyloric ligation procedure in the rat was designed by Shay et al., Gastroenterology, 5, 53 (1945) for the study of perforating gastric ulcers; however, as the method became known, it was also employed as a means of studying rat gastric secretion, Shay et al., Gastroenterology, 26, 906 (1954), Brodie, D. A., Am. J. Dig. Dis., 11,231 (1966). A modification of this procedure is presently used to evaluate compounds for gastric antisecretory activity.

Male Long Evans rats, 280–300 gm., are used. The animals are placed in individual cages and fasted for 24 hours with free access to water. Under ether anesthesia, the stomach is reached through a midline incision, and a cotton-thread ligature is placed around the pylorus. After wound closure, ether administration is stopped and either BL-5641, cimetidine or vehicle are administered intraperitoneally in a volume of 1 mg./kg. BL-5641 and cimetidine are solubilized with one equivalent of HCl and brought to the proper volume with water. The animals are returned to their cages from which the water bottles have been removed and two hours later are sacrificed with ether. The stomach is removed and the 2 hour gastric collection is drained into a graduated test tube for volume determination. Titratable acidity is measured by titrating a one ml. sample to pH 7.0 with 0.02N NaOH, using an Autoburet and an electrometric pH meter (Radiometer). Titratable acid output is calculated in microequivalents by multiplying the volume in milliliters by the acid concentration in milliequivalents per liter. The percent inhibition of acid output is calculated as follows $$\text{\% Inhibition Acid Output} = \frac{\text{Acid Output-Control} - \text{Acid Output-Drug}}{\text{Acid Output-Control}} \times 100$$

The results obtained with BL-5641 and cimetidine are presented in Table 2.

These results indicate that, in the two hour pylorus ligated rat preparation, BL-5641 is at least as potent as cimetidine with respect to the inhibition of gastric acid output.

TABLE 2

Effect of BL-5641 and Cimetidine on Gastric Acid Output in the Two Hour Pylorus Ligated Rat

| Compound | Dose (ip)[a] μMole/kg. | Dose (ip)[a] mg./kg. | % Inhibition of Acid Output | ED50 μMole/kg. |
|---|---|---|---|---|
| BL-5641 | 40 | 11.1 | 80 | |
| | 20 | 5.53 | 61 | ~11 |
| [Dimetidine] *Cimetidine* | 10 | 2.76 | 37 | |
| | 40 | 10 | 66 | |
| | 20 | 5 | 60 | ~14 |
| | 10 | 2.5 | 40 | |
| | 5 | 1.25 | 34 | |

[a]At least 5 animals were employed at each dose.

Determination of Gastric Antisecretory Activity in the Gastric Fistula Dog

Thomas type [Thomas, J. E., Proc. Soc. exp. Biol. Med., 46, 260 (1941)] stainless steel cannulae are inserted into the stomachs of beagle dogs (10–12 kg.) just orad to the pyloric gland area near the greater curvature to provide a chronic gastric fistula. Animals are allowed to recover for at least two months before any testing is done. Dogs are fasted overnight (~18 hours) with water ad lib prior to each experiment. The dogs are placed in a sling and an eight inch inside needle catheter (C. R. Baird, Inc.) with a 2 inch 17 gauge needle is inserted into a leg vein fior purposes of drug administration. Gastric secretions are collected every 15 minutes by gravity drainage from the opened cannula. Basal secretions are collected for two consecutive 15 minute periods and if these prove to be excessive (>4 ml./15 min.; pH <5.0) the animal is not used. A modification of the procedure described by Grossman and Konturek, Gastroenterology, 66, 517 (1974) was followed. Immediately after the second basal collection, histamine (100 μg./kg./hr.) is infused for 90 minutes with a Harvard Infusion Pump in a volume of 6 ml./hr. At this time either BL-5641, cimetidine (solubilized with one equivalent of HCl and brought a proper volume with normal saline) or normal saline is injected rapidly (within 30 seconds) in a volume of 0.1 ml./kg. and then infusion of histamine continues for an additional 150 minutes (total time of infusion is 4 hours). Each 15 minute sample of gastric juice is measured to the nearest 0.5 ml. and titratable acidity against 0.02N NaOH (endpoint pH 7.0) is measured with an Autoburet and pH meter (radiometer). The percent inhibition of acid output is calculated as described in the pylorus ligated rat procedure.

Equimolar doses of BL-5641 and cimetidine were administered to five different dogs and the results obtained are presented in Table 3.

Both BL-5641 and cimetidine produced an immediate inhibitory effect on gastric acid output. However, the degree of inhibition at equimolar doses was consistently greater and of longer duration with BL-5641 than with cimetidine. These results indicate that as an inhibitor of histamine-induced gastric acid output in the dog, BL-5641 is more potent and/or longer acting than cimetidine.

The invention is illustrated but in no way limited by the following Examples.

TABLE 3

Effect of BL-5641 and Cimetidine on Gastric Acid Output in Conscious Gastric Fistula Dogs

| Drug & Dose μM/kg. iv) | Dog No. | % Inhibition Acid Output (N = 1) 15 | 30 | 45 | 60 | 75 | 90 | 105 | 120 min. |
|---|---|---|---|---|---|---|---|---|---|
| BL-5641 (12) | 24136 | 66 | 99 | 99 | 99 | 99 | 93 | 91 | 73 |
| Cimetidine (12) | 24136 | 63 | 99 | 89 | 76 | 54 | 48 | 41 | 14 |
| BL-5641 (6) | 22619 | 82 | 99 | 99 | 95 | 78 | 76 | 52 | 53 |
| Cimetidine (6) | 22619 | 84 | 96 | 73 | 67 | 65 | 54 | 40 | 32 |
| BL-5641 (3) | 23606 | 60 | 59 | 36 | 34 | 32 | 42 | 24 | 0 |
| Cimetidine (3) | 23606 | 43 | 27 | 15 | 0 | 17 | 38 | 8 | 0 |
| BL-(5641) (1.5) | 24895 | 82 | 72 | 53 | 49 | 33 | 7 | 0 | 0 |
| Cimetidine (1.5) | 24895 | 73 | 57 | 60 | 29 | 0 | 18 | 0 | 0 |
| BL-5641 (0.75) | 23553 | 51 | 38 | 28 | 28 | 31 | 43 | 42 | 46 |
| Cimetidine (0.75) | 23553 | 50 | 10 | 24 | 17 | 35 | 27 | 25 | 19 |

EXAMPLE 1

N-Cyano-N'-{2-[(4-methyl-5-imidazolyl)methylthio]ethyl}-N''-propargylguanidine

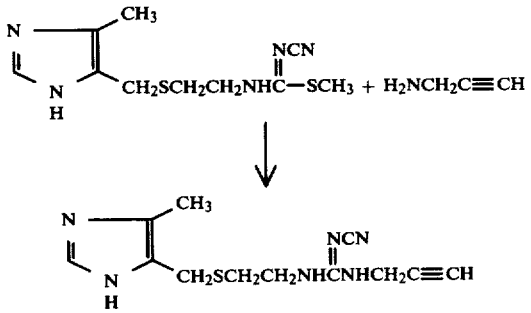

A mixture of N-cyano-N'-{2-[(4-methyl-5-imidazolyl)methylthio]ethyl}-S-methyl isothiourea (3.00 g, 0.0111 mole) and propargyl amine (2.50 g, 0.045 mole) in acetonitrile (60 ml) as stirred at reflux for 65 hours, and then was heated in a stainless steel pressure vessel at 120°-130° for 38 hours. The reaction mixture was cooled, decanted from a tar, and then evaporated to leave a gum (3.57 g). This material was placed on silica gel (100-200 mesh) and eluted with a mixture of methylene chloride (97 parts) and methanol (3 parts). The product obtained from a middle fraction was crystallized by trituration under acetonitrile, and then was recrystallized from acetonitrile to yield the title compound (0.236 g; 7.7%); m.p. 146°-149.5°.

Anal. Calc'd for $C_{12}H_{16}N_6S$: C, 52.15; H, 5.83; N, 30.41. Found: C, 51.86; H, 5.81; N, 30.70.

EXAMPLE 2

[N-Cyano-N'-{2-[(4-methyl-5-imidazolyl)methylthio]ethyl}-N''-propargylguanidine]

*N-Cyano-N'*-{2-[(4-methyl-5-unidazolyl)methylthio]ethyl}-N''-propargylguanidine

[A]

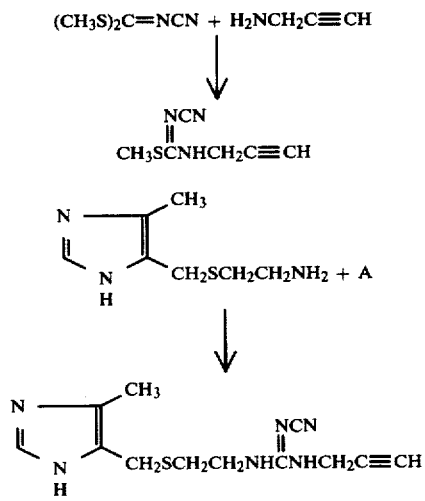

a. N-Cyano-N'-propargyl-S-methyl isothiourea (A)

A solution of dimethyl cyanodithioiminocarbonate (16.00 g, 0.109 mole) and propargyl amine (6.03 g, 0.109 mole) in acetonitrile (320 ml) was stirred at reflux for 4 hours, and then at 25° for 12 hours. Workup gave the title compound A (13.58 g, 81%), m.p. 160°-164°.

b. N-Cyano-N'-{2-[(4-methyl-5-imidazolyl)methylthio]ethyl}-N''-propargylguanidine A solution of A (11.71 g, 0.0765 mole) and 2-[(4-methyl-5-imidazolyl)methylthio] ethylamine (13.10 g, 0.0765 mole) in methanol (250 ml) was heated at reflux for 64 hours. The solvent was removed by evaporation, the residue placed on silica gel (100-200 mesh) and chromatographed by gradient elution using methylene chloride/methanol; the latter fractions yielded 4.0 g of the title compound. Recrystallization from acetonitrile gave purified product m.p. 150°-152.5° identical (ir, nmr, tlc) with the product prepared in Example 1.

EXAMPLE 3

N-Cyano-N'-{2-[(4-methyl-5-imidazolyl)methylthio]ethyl}-N''-(2-butyn-1-yl)guanidine

[B]

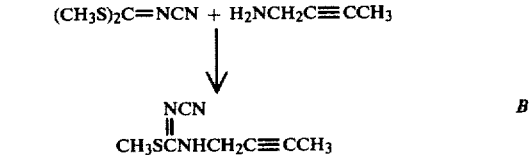

-continued

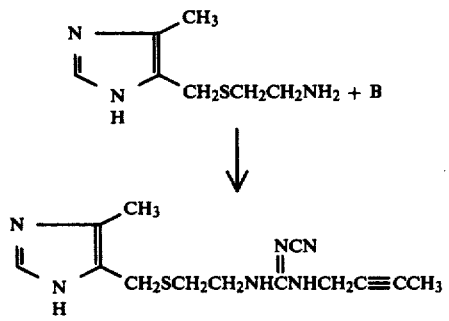

a. N-(2-Butyn-1-yl)-N'-cyano-S-methylisothiourea (B)

A solution of dimethyl cyanodithioiminocarbonate (10.00 g, 0.0684 mole) and 2-butyn-1-amine (4.73 g, 0.0684 mole) in acetonitrile (200 ml) was stirred at 25° for 0.5 hour, and then at reflux for 2.5 hours. The mixture was cooled, then filtered to yield the title compound B, m.p. 180°–183°.

b. N-Cyano-N'-{2-[(4-methyl-5-imidazolyl)methylthio]ethyl}-N''-(2-butyn-1-yl)guanidine A solution of B (6.82 g, 0.0407 mole) and 2-[(4-methyl-5-imidazolyl)methylthio] ethylamine (6.98 g, 0.0407 mole) in methanol (140 ml) was heated at reflux for 40 hours. Workup and chromatography as described above for Example 2 yielded the title compound. When the title compound was prepared according to the general procedure of Example 1, it melted at 128°–130°.

EXAMPLE 4

N-Cyano-N'-{2-[(4-methyl-5-imidazolyl)methylthio]ethyl}-N''-(3-butyn-1-yl)guanidine The general procedure of Example 1 is repeated except that the propargyl amine utilized therein is replaced by an equimolar amount of 3-butyn-1-amine, and the title product is thereby produced.

EXAMPLE 5

N-Cyano-N'-{2-[(4-methyl-5-imidazolyl)methylthio]ethyl}-N''-(4-pentyn-1-yl)guanidine The general procedure of Example 1 is repeated except that the propargyl amine utilized therein is replaced by an equimolar amount of 4-pentyn-1-amine, and the title product is thereby produced; m.p. 99°–103°.

[EXAMPLE 6]

[N-Cyano-N'-{2-[(4-methyl-5-imidazolyl)methylthio]ethyl}-N''-(2-methyl-3-butyn-2-yl)guanidine]

[The general procedure of Example 3 is repeated except that the 2-butyn-1-amine utilized therein is replaced by an equimolar amount of 1,1-dimethylpropargylamine, and the title product is thereby produced.]

EXAMPLE 7

N-Cyano-N'-{2-[(4-methyl-5-imidazolyl)methylthio]ethyl)-N''-(3-butyn-2-yl)guanidine The general procedure of Example 3 is repeated except that the 2-butyn-1-amine utilized therein is replaced by an equimolar amount of 1-methylpropargylamine, and the title product is thereby produced.

EXAMPLE 8

N-Cyano-N'-{2-[(4-methyl-5-imidazolyl)methylthio]ethyl}-N''-(2-butyn-1-yl)guanidine A mixture of N-cyano-N'-{2-[(4-methyl-5-imidazolyl)methylthio]ethyl}-S-methylisothiourea (3.00 g. 0.0111 mole) and 2-butyne-1-amine (3.07 g., 0.0445 mole) in 60 ml. of propionitrile was stirred at reflux for 40 hours. TLC assay of an aliquot of the reaction mixture showed a trace of the isothiourea starting material, so the mixture was refluxed for an additional 6 hours and then stirred at room temperature for 64 hours. The solvent (along with excess amine) was removed at reduced pressure and the residual gum was placed on silica gel (100–200 mesh) and eluted with a mixture of methylene chloride (97 parts) and methanol (3 parts). The middle fractions were combined and evaporated to give 1.81 g. of yellow gum. The gum was dissolved in 20 ml. of ethyl acetate and crystallized at −15° C. The resulting pale yellow solid (1.2 g.) was dissolved in 11 ml. of hot acetonitrile and recrystallized at −15° C.; yield 1.072 g., m.p. 128°–130° C.

Anal. Calc'd for $C_{13}H_{18}N_6S$: C, 53.77; H, 6.25; N, 28.94; S, 11.08. Found: C, 53.72; H, 6.29; N, 29.62; S, 11.34.

EXAMPLE 9

N-Cyano-N'-{2-[(4-methyl-5-imidazolyl)methylthio]ethyl}-N''-(3-butyn-1-yl)guanidine A mixture of N-cyano-N'-{2-[(4-methyl-5-imidazolyl)methylthio]ethyl}-S-methylisothiourea (3.00 g., 0.0111 mole) and 3-butyn-1-amine (3.13 g., 0.453 mole) in 60 ml. of propionitrile was stirred at reflux for 40 hours. The solvent was evaporated to give 5.40 g. of a syrup which was placed on 70 g. of 100–200 mesh silica gel and chromatographed by gradient elution using methylene chloride/methanol.

| Fraction | Eluant | Volume | Weight |
|---|---|---|---|
| 1 | 99 $CH_2Cl_2$/1 MeOH | 100 ml. | — |
| 2 | " | 70 ml. | — |
| 3 | " | 50 ml. | 0.117 g. |
| 4 | " | 30 ml. | — |
| 5 | " | 75 ml. | 0.067 g. |
| 6 | " | 150 ml. | 0.080 g. |
| 7 | " | 325 ml. | 0.168 g. |
| 8 | 98 $CH_2CH_2$/2 MeOH | 50 ml. | — |
| 9 | " | 150 ml. | 0.125 g. |
| 10 | " | 250 ml. | 0.811 g. |
| 11 | " | 250 ml. | 0.72 g. |
| 12 | 97 $CH_2CH_2$/3 MeOH | 175 ml. | 0.125 g. |
| 13 | " | 225 ml. | 0.133 g. |
| 14 | " | — | 0.027 g. |
| 15 | " | 225 ml. | 0.002 g. |
| 16 | " | 200 ml. | |
| 17 | 95 $CH_2CH_2$/5 MeOH | 250 ml. | 0.035 g. |
| 18 | " | 250 ml. | 0.236 g. |

TLC (silica gel, 90 $CH_2Cl_2$/10 MeOH) indicated fractions 9–12 were pure and should be combined. Fractions 1–8 showed fast moving impurities. Fractions 13 and 14 showed some trailing impurities. Fractions 9–12 were combined and evaporated to 1.72 g. of a yellow gum. The gum was dissolved in 11 ml. of nitromethane and crystallized at −15° C. (pale yellow solid, 1.18 g.), which was recrystallized from 9 ml. of nitromethane to give 0.987 gm.; m.p. 86°–89° C. (softens at 85° C.). Infrared and NMR (100 MHZ) were clean and consistent with the desired structure. NMR showed that the product was solvated with approximately 0.08 mole of nitromethane.

Anal. Calc'd for $C_{13}H_{18}N_6S.0.08$ ($CH_3NO_2$): C, 53.21; H, 6.22; N, 28.84; S, 10.86.

Found: C, 52.68, 52.87; H, 6.28, 6.02, N, 29.39, 29.50; S, 11.22.

EXAMPLE 10

N-Cyano-N'-{2-[(4-methyl-5-imidazolyl)methylthio]ethyl}-N''-(4-pentyn-1-yl)guanidine A mixture of N-cyano-N'-{2-[(4-methyl-5-imidazolyl)methylthio]ethyl}-S-methylisothiourea (3.00 g., 0.0111 mole) and 4-pentyn-1-amine (3.69 g., 0.0445 mole) in 60 ml. of acetonitrile was stirred at reflux for 24 hours, and then allowed to stand at room temperature for 96 hours. The solvent and excess amine were removed under reduced pressure and the residual yellow gum was purified by chromatography on 50 g. of 100–200 mesh silica gel, using gradient elution with methylene chloride/methanol (99:1–96:4). The middle fractions indicated by TLC to be pure were combined and evaporated to give 1.91 g. of yellow gum which was crystallized at −15° C. from 18 ml. of ethyl acetate. The resulting white solid (1.25 g.) was recrystallized at −15° C. from 10 ml. of acetonitrile to give 1.063 g. of product; m.p. 99°–103° C.

Anal. Calc'd for $C_{14}H_{20}N_6S$: C, 55.24; H, 6.52, N, 27.61; S, 10.53. Found: C, 55.43; H, 6.58, N, 28.26; S, 10.97.

We have recently found that, in the preparation of N-cyano-N'-{2-[(4-methyl-5-imidazolyl)methylthio]ethyl}-N''-propargylguanidine via Reaction Scheme I, selected reaction conditions in the last step thereof give greatly improved yields of product as well as a product containing less impurities. The latter condition has the added advantage of permitting the initial ("crude") product to be isolated as a crystalline solid which may be more highly purified by simple recrystallization, and avoids the chromatographic purification of the initial crude product which we previously considered desirable when using other reaction conditions.

The selected reaction conditions referred to above consist of using methanol as solvent, utilizing a more concentrated solution in the reaction (approximately 1 gram of the substituted isothiourea per 5 ml of methanol), the use of a nitrogen sweep of the reaction apparatus during the reaction, and the utilization of freshly distilled propargylamine in the reaction.

Experiments have shown that the use of a nitrogen sweep during the reaction avoids the formation of small amounts of two as yet unidentified by-products which are formed in the absence of a nitrogen sweep. These by-products, when present, resisted removal by column chromatography and recrystallization. It is believed that the nitrogen sweep prevents the formation of these by-products by removing the methyl mercaptan gas as quickly as it is formed.

The increased yield of N-Cyano-N'-{2-[(4-methyl-5-imidazolyl)methylthio]ethyl}-N''-propargylguanidine obtained by utilizing the above-described conditions is shown in the following Examples but it is not intended that the invention be limited in any way to their use.

EXAMPLE 11

N-Cyano-N'-{2-[(4-methyl-5-imidazolyl)methylthio]ethyl}-N''-propargylguanidine The mixture of N-cyano-N'-{2-[(4-methyl-5-imidazolyl)methylthio]ethyl}-S-methylisothiourea (10.0 g; 0.0371 mole) and distilled propargylamine (20 ml; 0.325 mole) in methanol (50 ml) was stirred at reflux, under a positive pressure nitrogen atmosphere (nitrogen sweep), for 20.5 hours. The solvent and excess amine were then removed by evaporation to leave a yellow-brown oil that readily crystallized. Trituration of the crude product under isopropanol (30 ml) gave the title compound as an off-white, friable solid (8.11 g, 79%); m.p. 146°–148.5°.

EXAMPLE 12

N-Cyano-N'-{2-[(4-methyl-5-imidazolyl)methylthio]ethyl}-N''-propargylguanidine A mixture of N-cyano-N'-{2-[(4-methyl-5-imidazolyl)methylthio]ethyl}-S-methylisothiourea (100 g; 0.371 mole) and distilled propargylamine (150 ml; 2.44 moles) in methanol (500 ml) was stirred at reflux under a positive pressure nitrogen atmosphere (nitrogen sweep) for 22 hours. The reaction mixture was cooled, and the solvent and excess amine were removed by evaporation to leave an amber oil that readily crystallized. The crude product was triturated under isopropanol (250 ml), cooled at 0° for 2 hours and collected by filtration. The filter cake was washed with cold isopropanol and dried in vacuo over $P_2O_5$ for 16 hours. The dried title product was a near-white dense solid; yield 73.5 gm (71.7%) m.p. 147°–149°.

EXAMPLE 13

Recrystallization of N-Cyano-N'-{2-[(4-methyl-5-imidazolyl)methylthio]ethyl}-N''-propargylguanidine The final products obtained in Examples 11 and 12 were combined (total 81.3 g,) dissolved in hot isopropanol (1000 ml), filtered through "Super-Cel" and allowed to cool at room temperature for ca. 68 hours. The resulting crystalline product was recovered by filtration, washed with cold isopropanol, pulverized and dried in a heated desiccator under high vacuum for ca. 45 hours. Yield 72.4 g (89% recovery); m.p. 149°–151°. HPLC assay showed the purity to be ca. 99.5% The NMR (100 MHz) spectrum was clean and consistent.

Anal. Calc'd for $C_{12}H_{16}N_6S$: C, 52.15; H, 5.83; N, 30.41; S, 11.60. Found: C, 52.42; H, 5.94; N, 30.51; S, 11.35.

We claim:

1. A compound of the formula

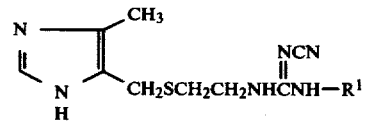

wherein $R^1$ is a straight or branched chain alkynyl group containing from 3 to 9 carbon atoms, inclusive, or a nontoxic pharmaceutically acceptable acid addition salt thereof.

2. A compound of the formula

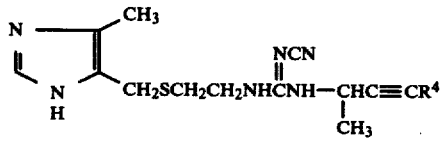

wherein $R^4$ is hydrogen or methyl, or a nontoxic pharmaceutically acceptable acid addition salt thereof.

3. A compound of the formula

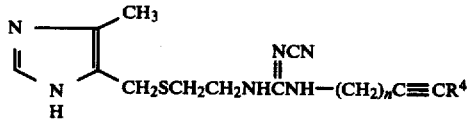

wherein $R^4$ is hydrogen or methyl and n is an integer of from 1 to 6, inclusive, or a noxtoxic pharmaceutically acceptable acid addition salt thereof.

[4. A compound of the formula

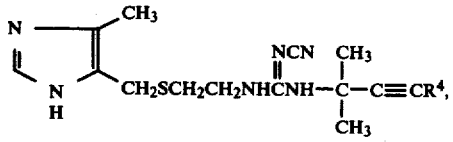

wherein $R^4$ is hydrogen or methyl, or a nontoxic pharmaceutically acceptable acid addition salt thereof.]

5. N-Cyano-N'-{2-[(4-methyl-5-imidazolyl)methylthio]ethyl}-N''-propargylguanidine or a nontoxic pharmaceutically acceptable acid addition salt thereof.

6. N-Cyano-N'-{2-[(4-methyl-5-imidazolyl)methylthio]ethyl}-N''-propargylguanidine.

7. A nontoxic pharmaceutically acceptable salt of N-cyano-N'-{2-[(4-methyl-5-imidazolyl)methylthio]ethyl}-N''-propargylguanidine.

8. N-Cyano-N'-{2-[(4-methyl-5-imidazolyl)methylthio]ethyl}-N''-(2-butyn-1-yl)guanidine or a nontoxic pharmaceutically acceptable acid addition salt thereof.

9. N-Cyano-N'-{2-[(4-methyl-5-imidazolyl)methylthio]ethyl}-N''-(3-butyn-1-yl)guanidine or a nontoxic pharmaceutically acceptable salt thereof.

10. N-Cyano-N'-{2-[(4-methyl-5-imidazolyl)methylthio]ethyl}-N''-(4-pentyn-1-yl)guanidine or a nontoxic pharmaceutically acceptable acid addition salt thereof.

[11. N-Cyano-N-'-{2-[(4-methyl-5-imidazolyl)methylthio]ethyl}-N''-(2-methyl-3-butyn-2-yl)guanidine or a nontoxic pharmaceutically acceptable acid addition salt thereof.]

12. N-Cyano-N'-{2-[(4-methyl-5-imidazolyl)methylthio]ethyl}-N''-(3-butyn-2-yl)guanidine or a nontoxic pharmaceutically acceptable acid addition salt thereof.

* * * * *

UNITED STATES PATENT AND TRADEMARK OFFICE

CERTIFICATE OF CORRECTION

PATENT NO. : Re. 31,588

DATED : May 22, 1984

INVENTOR(S) : Ronnie Ray Crenshaw and George Michael Luke

It is certified that error appears in the above-identified patent and that said Letters Patent is hereby corrected as shown below:

Column 5, lines 37-41, Place brackets around the paragraph as follows: [Another more preferred embodiment of the invention is N-cyano-N'-{2-[(4-methyl-5-imidazolyl) methylthio]ethyl} -N"-(2-methyl-3-butyn-2-yl) guanidine or a non-toxic pharmaceutically acceptable acid addition salt thereof.]

Column 7, line 64 "chistamine" should read -- histamine --

Column 8, line 5 "or" should read -- of --

Column 10, line 59 "fior" should read -- for --

Column 11, line 32 Table 3, left heading, "uM/kg. iv)" should read -- (uM/kg.iv) --

Column 11, line 38 Table 3 "BL-(5641)" should read -- BL-5641 --

Column 11, line 64 "as" should read -- was --

UNITED STATES PATENT AND TRADEMARK OFFICE

CERTIFICATE OF CORRECTION

PATENT NO. : Re. 31,588

DATED : May 22, 1984

INVENTOR(S) : Ronnie Ray Crenshaw and George Michael Luke

It is certified that error appears in the above-identified patent and that said Letters Patent is hereby corrected as shown below:

Column 12, line 11 delete "[" before "N-cyano"

Column 12, line 12 add "[" before "proparglyguanidine"

Column 12, line 12 insert after "]", the term -- propargylguanidine --

Column 12, lines 13-14 delete "N-Cyano-N'-{2-[(4-methyl-5-unidazolyl)methylthio]ethyl}-N"-propargylguanidine"

Column 14, line 48 "$CH_2CH_2$/2MeOH" should read -- $CH_2Cl_2$/2MeOH --

Column 14, line 51 "$CH_2CH_2$/3MeOH" should read -- $CH_2Cl_2$/3MeOH --

Column 14, line 56 "$CH_2CH_2$/5MeOH" should read -- $CH_2Cl_2$/5MeOH --

Column 14, line 68 "(100 MHZ)" should read -- (100 MHz) --

UNITED STATES PATENT AND TRADEMARK OFFICE

CERTIFICATE OF CORRECTION

PATENT NO. : Re. 31,588

DATED : May 22, 1984

INVENTOR(S) : Ronnie Ray Crenshaw and George Michael Luke

It is certified that error appears in the above-identified patent and that said Letters Patent is hereby corrected as shown below:

Column 15, line 6 "H, 6.28, 6.02," should read -- H, 6.28, 6.02; --

Column 15, line 31 "6.52," should read -- 6.52; --

Column 15, line 32 "6.58," should read -- 6.58; --

Signed and Sealed this

Sixth Day of November 1984

[SEAL]

*Attest:*

*Attesting Officer*

GERALD J. MOSSINGHOFF

*Commissioner of Patents and Trademarks*